United States Patent [19]

Olah

[11] 4,419,528
[45] Dec. 6, 1983

[54] REGIOSELECTIVE PREPARATION OF α- OR β-NAPHTHOL

[75] Inventor: George A. Olah, Beverly Hills, Calif.

[73] Assignee: PCUK - Produits Chimiques Ugine Kuhlmann, Courbevoie, France

[21] Appl. No.: 82,152

[22] Filed: Oct. 5, 1979

[51] Int. Cl.$^3$ .............................................. C07C 37/60
[52] U.S. Cl. .................................... 568/741; 568/803
[58] Field of Search ....................... 568/741, 771, 803

[56] References Cited

U.S. PATENT DOCUMENTS 3,461,170  8/1970  Schmerling ....................... 568/741
3,600,447  8/1971  Vesely .............................. 568/741
3,816,545  6/1974  Bloch ............................... 568/741

OTHER PUBLICATIONS

Davies et al., "J. Chemical Soc." London (1961) p. 3116 +.
Kovacic et al., "J. Organic Chemistry" vol. 31 (1966) 2001 +.
Vesely et al., "J. Organic Chemistry" vol. 35 (1970) p. 4028 +.
Olah, "Friedel–Crafts Chemistry" Wiley & Sons, NY 1973, pp. 367–371.
Olah et al., "Science" Reprint Series Oct. 5, 1979 vol. 206, pp. 13–20.

*Primary Examiner*—Werren B. Lone
*Attorney, Agent, or Firm*—Pennie & Edmonds

[57] ABSTRACT

A process for the selective preparation of α- or β-naphthol, respectively, by acid (Lewis or Bronsted, or superacidic mixtures thereof) catalyzed hydroxylation of naphthalene with hydrogen peroxide. Conventional (non-superacidic) acid systems, such as hydrogen fluoride, pyridine-hydrogen fluoride complexes (i.e., pyridinium polyhydrogen fluoride), anhydrous aluminum chloride, and the like give α-naphthol regioselectivity in isomeric purity of 92 to 98+%. The use of superacidic systems, such as fluorosulfuric acid, fluorosulfuric acid-antimony pentafluoride, hydrogen fluoride-boron trifluoride, hydrogen fluoride-antimony pentafluoride, hydrogen fluoride, tantalum pentafluoride, and the like, result, on the other hand, in the formation of β-naphthol in 92–98% isomeric purity.

8 Claims, No Drawings

REGIOSELECTIVE PREPARATION OF α- OR β-NAPHTHOL

TECHNICAL FIELD

A process for the selective preparation of α- or β-naphthol, respectively, by acid (Lewis or Bronsted, or superacidic mixtures thereof) catalyzed hydroxylation of naphthalene with hydrogen peroxide.

BACKGROUND ART

Naphthols are generally prepared from the corresponding isomeric isopropylnaphthalene hydroperoxides by the Hock process, from isomeric naphthalenesulfonic acids by alkali hydrolysis or from naphthylamines by acidic hydrolysis. Due to the necessity of using large excess of acid or alkali, as well as limitations in the availability and expensiveness of pure isomeric α- and β-precursors, respectively, as well as the potentially carcinogenic nature of some of them, neither method is entirely satisfactory.

Only perfunctory studies have so far been reported on the direct hydroxylation of naphthalene. The reaction of aroyl peroxides with naphthalene via homolytic substitution giving mixtures of naphthols was reported by Davies, Hey and Williams (Journal Chemical Society (London), 1961, 3116. Friedel-Crafts type oxygenation of naphthalene with diisopropyl peroxydicarbonate gave a low yield of naphthols (Kovacic and Kurz, Journal or Organic Chemistry, Vol 31, 1966, 2001). In the reaction of 30% $H_2O_2$ with naphthalene in HF in the presence of $CO_2$ at superatmospheric pressure and at 4°-11° C., 30% α- and 9% β-naphthol were obtained together with 17% 1,5-naphthalenediol and 35% of higher boiling and polymeric materials. (Vesely and Schmerling, Journal of Organic Chemistry, Vol. 35, 1970, 4028. This publication also reports that, in the absence of carbon dioxide, the product consisting only of high-melting, black, alkali soluble resinous material. High selectivity of α-naphthol is obtained with conventional acid systems, such as hydrogen fluoride in the absence of carbon dioxide, according to the present invention and contrary to the teachings of the Vesely et al. publication. None of these reactions are, thus, suitable for regioselectively producing α- or β-naphthol.

DISCLOSURE OF THE INVENTION

The present invention is based on the unexpected discovery that the acid catalyzed hydroxylation of naphthalene with highly concentrated hydrogen peroxide (in concentrations between 30-90%, preferentially 90%), depending on the acidity (superacidity) of the systems used, gives either α- or β-naphthol as the regioselective product of the reactions in isomeric purity of up to and in excess of 98%.

DETAIL DESCRIPTION OF THE INVENTION

The regioselective preparation of α- and β-naphthol from naphthalene with hydrogen peroxides requires the reaction to be carried out in suitable acid systems, generally at atmospheric pressure or at pressures not exceeding 10 atm, at temperatures ranging from −100° to 100° C., preferentially between −78° and 20° C. The regioselectivity of the reaction is primarily dependent on the nature and strength of the acid system employed in conjunction with other conditions specified, such as temperature and concentration of hydrogen peroxide.

When carrying out the hydroxylation of naphthalene with a molar excess of $H_2O_2$ (90%) in a conventional acid system, such as anhydrous hydrogen fluoride, at temperatures ranging from −10° to 0° C. and at atmospheric or slightly superatmospheric pressure, 42.3% α-naphthol and only 0.7% β-naphthol were obtained, with about 9% of polymeric higher molecular weight product and 48% of naphthalene can be recovered unchanged. The yield of α-naphthol is 81% with an isomeric purity of 98.4%.

Using convenient anhydrous hydrogen fluoride-pyridine complex as the acidic reaction medium at atmospheric pressure and at ambient temperature, the reaction of naphthalene with a molar excess of hydrogen peroxide at 10° to 20° C. gave 25.3% α-naphthol with 0.4% β-naphthol, 9.5% dihydroxynaphthalenes, and 1.2% higher molecular weight polymeric materials were formed with 47% naphthalene recovered unchanged. The yield of α-naphthol is 47%, with an isomeric purity of 98.4%.

Unexpectedly and in sharp contrast, it was discovered that when carrying out the reaction of naphthalene with hydrogen peroxide (90% solution) in superacid media, such as in hydrogen fluoride, saturated with boron trifluoride, at temperatures around −50° C., 52% β-naphthol and 0.7% of α-naphthol were obtained, (together with some 18% of dihydroxynaphthalenes and 12% polymeric higher molecular weight materials), corresponding to a 60% yield of β-naphthol in 98.7% isomeric purity.

When carrying out the reaction in other superacidic systems, similarly high regioselective preparation of β-naphthol was achieved. For example, in fluorosulfuric acid solution at a temperature of −78° to −70° C., naphthalene yielded 37% of β-naphthol with 3% of a α-naphthol, 17% dihydroxynaphthalenes and 5% higher molecular weight polymeric materials. 39% naphthalene was recovered. The yield of β-naphthol corresponds to 61%, with an isomeric purity of 92.5%.

Using a 1:1 molar mixture of fluorosulfuric acid and antimony pentafluoride diluted with sulfuryl chloride fluoride, a solvent of low nucleophilicity, the reaction of naphthalene with hydrogen peroxide (90% solution) at temperatures between −78° and −70° C., gave 54.2% of β-naphthol with 4.4% of α-naphthol. About 6% of dihydroxynaphthalenes were also formed with only traces of polymeric material and 22% naphthalene was recovered. The yield of β-naphthol is 69% with an isomeric purity of 92.5%. Similar results showing high regioselectivity in the formation of β-naphthol were also obtained in other superacidic systems, such as in hydrogen fluoride-antimony pentafluoride, hydrogen fluoride-tantalum pentafluoride, trifluoromethanesulfonic acid-antimony pentafluoride, and the like.

Table I summarizes data, based on the specific examples detailed subsequently, showing the remarkable regioselectivity obtained in the acid catalyzed hydroxylation of naphthalene with hydrogen peroxide, depending on the nature of the acid systems employed. The high and unexpected regioselectivity observed is considered to be a consequence of the acidity of the systems employed. The acidity of anhydrous hydrogen fluoride on the logarithmic Hammett $H_o$ acidity function scale is −10. Fluorosulfuric acid has a value of about −14.5, whereas 1:1 molar fluorosulfuric acid-antimony pentafluoride or hydrogen fluoride-antimony pentafluoride have strengths of about −20 to −22. In these latter superacids, naphthalene is protonated to the naphthalenium ion, as shown by nuclear magnetic resonance spectroscopic studies of the solutions. It is this latter species which is then hydroxylated in the now preferred β-position by hydrogen peroxide. In contrast, in the weaker conventional acid systems (comparable or less acidic than 100% sulfuric acid, $H_o = -11$, below which acids are considered to be superacids), naphthalene is hydroxylated in its unprotonated form giving predominantly the α-isomer. The term "in excess of $-11$" as used herein means numbers of lesser numerical value, such as $-14.5$, $-20$, etc., and "less than $-11$" would be numbers of greater numerical value, such as $-9$.

It was established in control experiments that no isomerization of α- and β-naphthol to each other takes place under any of the acidic conditions employed in the reactions.

The scope of the invention is further described in connection with the following examples, which are set forth for the purpose of illustration and are not to be considered to limit the scope of the invention in any manner.

EXAMPLE 1

Naphthalene (0.05 mol) in 75 ml anhydrous hydrogen fluoride was reacted with a solution of 0.06 mol of $H_2O_2$ (90% solution) in 100 ml of anhydrous hydrogen fluoride at a temperature between $-10°$ to $0°$ C. The reaction mixture was stirred for 2 hours at this temperature; then it was quenched with ice water and extracted with ether. The ether solution was washed with water and naphthols extracted with 10% sodium hydroxide solution. Distillation of the ether layer allowed recovery of 52% of unreacted naphthalene, with about 5% polymeric material remaining. After acidification and extraction with ether of the caustic solution, the solution was distilled to isolate products. Analysis of isomeric naphthols was carried out by gas-liquid chromatography after first converting to convenient trimethylsilyl ethers by N,O-bis(trimethylsilyl)trifluoroacetamide.

Product analysis showed 42.3% α- and 0.7% β-naphthol corresponding to a conversion of 43% and a yield of 81%. Isomeric purity of α-naphthol is 98.4%.

EXAMPLE 2

To an ice-cooled solution of naphthalene (0.05 mol) in 75 ml of 2.5:1 w/w anhydrous hydrogen fluoride-pyridine complex was added with good stirring a solution of 0.06 mols of $H_2O_2$ (30% solution) in 50 ml of HF-pyridine. The reaction mixture was stirred at $0°$ C. for two hours, and subsequently for an additional hour at room temperature. It was then poured on ice water and extracted with ether. The ether solution was washed with water and naphthols extracted with a 10% sodium hydroxide solution. The organic layer upon evaporation of the solvent allowed recovery of 47% of unchanged naphthalene with 1.2% of higher molecular weight polymeric material. Product analysis showed 25.3% α-naphthol and 0.4% β-naphthol, together with 9.5% of dihydroxynaphthalenes.

EXAMPLE 3

Well pulverized naphthalene (0.1 mol) was dissolved in 150 ml anhydrous hydrogen fluoride saturated with boron trifluoride at $-78°$ C., forming a clear red solution. Separately, a solution of 0.12 mol of $H_2O_2$ (90% solution) was prepared in 50 mol of anhydrogen fluoride saturated with boron trifluoride at $-78°$ C. The latter solution was carefully added at $-50°$ C. with good stirring to the solution of naphthalene and stirred at this temperature for an additional hour. The reaction mixture was then quenched with ice water and extracted with ether. Workup and product analysis was carried out as described in Example 1. 14% naphthalene was recovered unchanged with 52% of β-naphthol and 0.7% α-naphthol being obtained together with 18% of dihydroxynaphthalenes and 12% polymeric material.

EXAMPLE 4

To a vigorously stirred suspension of 0.1 mol of naphthalene in 100 ml of fluorosulfuric acid at $-78°$ C. was added an equally cold solution of 0.12 mol of $H_2O_2$ (90% solution) in 100 ml of fluorosulfuric acid. The reaction mixture was stirred for 30 minutes, then quenched with ice water, and worked up and analyzed as in Example 1. 39% naphthalene was recovered unchanged. 37% of β-naphthol and 3% of α-naphthol were obtained, together with 17% of dihydroxynaphthalenes and 5% polymeric material.

EXAMPLE 5

0.1 mol of naphthalene was dissolved at $-78°$ C. in a solution of 50 ml of 1:1 mol/mol $FSO_3H$—$SbF_5$ in 100 ml of sulfuryl chloride fluoride. 0.12 mol of $H_2O_2$ (90% solution) was separately dissolved in a solution of 50 ml of 1:1 (m/m) $FSO_2H$—$SbF_5$ and 100 ml of sulfuryl chloride fluoride at the same temperature. The $H_2O_2$ superacid solution was carefully added with good stirring at $-78°$ to $-70°$ C. to the superacid solution of naphthalene and the reaction mixture subsequently was stirred for an additional 30 minutes, then quenched with ice water, worked up, and analyzed as in Example 1. 22% naphthalene was recovered unchanged. 54.2% of β-naphthol and 4.4% of naphthol were obtained, together with 6% dihydroxynaphthalenes and only traces of polymeric material.

EXAMPLE 6

Reaction was carried out as in Example 3, but using a solution of anhydrous hydrogen fluoride and antimony pentafluoride, in a mole ratio of 4 to 1. 49% of β-naphthol was obtained together with 0.6% of α-naphthol, 13% of dihydroxynaphthalenes, and 9% polymeric material.

EXAMPLE 7

Reaction was carried out as in Example 5, but using a solution of HF-$TaF_5$ (5:1 mole ratio). 39% of β-naphthol was obtained, together with 0.4% of α-naphthol, 10% dihydroxynaphthalenes and 5% polymeric material.

TABLE I

Regioselectivity in the Acid Catalyzed Hydroxylation of Naphthalene with Hydrogen Peroxide

| Acid System | Example | Reaction Temp °C. | % Yield of Naphthols | % Isomer Composition | |
|---|---|---|---|---|---|
| | | | | α- | β- |
| HF | 1 | $-10$–$0°$ | 43 | 98.4 | 1.6 |
| 70% HF-30% pyridine | 2 | $0$–$+20°$ | 25.7 | 98.4 | 1.6 |
| HF-$BF_3$ | 3 | $-78$ | 52.7 | 1.3 | 98.7 |
| $FSO_3H$ | 4 | $-78$–$70°$ | 40.0 | 7.5 | 92.5 |
| $FSO_3H$-$SbF_5$ | 5 | $-78$–$70°$ | 58.6 | 7.5 | 92.5 |
| HF-$SbF_5$ | 6 | $-78$–$70°$ | 49.6 | 1.2 | 98.2 |

TABLE I-continued

Regioselectivity in the Acid Catalyzed Hydroxylation of Naphthalene with Hydrogen Peroxide

| Acid System | Example | Reaction Temp °C. | % Yield of Naphthols | % Isomer Composition α- | β- |
|---|---|---|---|---|---|
| HF-TaF$_5$ | 7 | −70° | 39.4 | 3.0 | 97.0 |

I claim:

1. A process for the regioselective hydroxylation of naphthalene with hydrogen peroxide giving either α- or β-naphthol in high isomeric purity between about 92 and 98+% depending on the acid system employed to carry out the reaction which comprises reacting naphthalene with a molar excess of hydrogen peroxide in an acid system having an H$_o$ acidity function of −11 or less to produce α-naphthol with an isomeric purity between about 92 and 98+% or in a superacidic system having an H$_o$ acidity function in excess of −11 to produce β-naphthol with an isomeric purity between about 92 and 98+%.

2. A process for the regioselective hydroxylation of naphthalene having an α-naphthol isomeric purity between about 92 and 98+% which comprises reacting naphthalene with a molar excess of hydrogen peroxide in an acid system having an H$_o$ acidity function of −11 or less at a temperature between about −10° C. and 20° C.

3. The process of claim 2 in which the acid system comprises hydrogen fluoride or complexes of hydrogen fluoride with pyridine.

4. A process for the selective hydroxylation of naphthalene to β-naphthol having an isomeric purity between about 92 and 98+% which comprises reacting naphthalene with a molar excess of hydrogen peroxide in a superacidic system having an H$_o$ acidity function in excess of −11.

5. The process of claim 4 in which the temperature of the reaction is between about −78° C. and 20° C.

6. The process of claim 1 or 2 in which the hydrogen peroxide concentration is about 90%.

7. The process of claims 5 or 6 in which the hydrogen peroxide concentration is about 90%.

8. The process of claims 5 or 6 in which the superacidic system comprises hydrogen fluoride-boron trifluoride, hydrogen fluoride-antimony pentafluoride, hydrogen fluoride-tantalum pentafluoride, hydrogen fluoride-niobium pentafluoride, fluorosulfuric acid, fluorosulfuric acid-antimony pentafluoride, fluorosulfuric acid-tantalum pentafluoride, fluorosulfuric acid-niobium pentafluoride, trifluoromethanesulfonic acid-antimony pentafluoride or trifluoromethanesulfonic acid-tantalum pentafluoride.

* * * * *

UNITED STATES PATENT AND TRADEMARK OFFICE
CERTIFICATE OF CORRECTION

PATENT NO. : 4,419,528
DATED : December 6, 1983
INVENTOR(S) : George A. Olah

It is certified that error appears in the above—identified patent and that said Letters Patent is hereby corrected as shown below:

The title of the application reads "α- OR β- NAPHTHOL" and should read --ALPHA- OR BETA-NAPHTHOL--.

Column 1, line 30, reads "Journal or Organic" and should read --Journal of Organic--.

Column 6, lines 16 and 18, read "claims 5 or 6", and should read --claims 4 or 5--.

Signed and Sealed this

Eighth Day of May 1984

[SEAL]

Attest:

GERALD J. MOSSINGHOFF

Attesting Officer

Commissioner of Patents and Trademarks